US009645147B2

(12) United States Patent
Sedegah et al.

(10) Patent No.: US 9,645,147 B2
(45) Date of Patent: May 9, 2017

(54) RECOMBINANT POLYPEPTIDE CONSTRUCT COMPRISING *PLASMODIUM FALCIPARUM* CIRCUMSPOROZOITE PROTEIN HLA CLASS I RESTRICTED T-CELL EPITOPES

(71) Applicants: Martha Sedegah, Gaithersburg, MD (US); Thomas Richie, Glenelg, MD (US)

(72) Inventors: Martha Sedegah, Gaithersburg, MD (US); Thomas Richie, Glenelg, MD (US)

(73) Assignee: The United States of America as Represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 14/069,656

(22) Filed: Nov. 1, 2013

(65) Prior Publication Data
US 2015/0125482 A1   May 7, 2015

(51) Int. Cl.
*A61K 39/015* (2006.01)
*A61K 39/02* (2006.01)
*A61K 39/00* (2006.01)
*G01N 33/569* (2006.01)
*G01N 33/50* (2006.01)
*C07K 14/445* (2006.01)

(52) U.S. Cl.
CPC ..... *G01N 33/56905* (2013.01); *A61K 39/015* (2013.01); *C07K 14/445* (2013.01); *G01N 33/505* (2013.01); *G01N 2333/445* (2013.01)

(58) Field of Classification Search
CPC ..... A61K 39/00; A61K 39/002; A61K 39/015
USPC .......... 424/184.1, 185.1, 234.1, 269.1, 272.1
See application file for complete search history.

(56) References Cited

U.S. PATENT DOCUMENTS

| | | | |
|---|---|---|---|
| 2002/0119127 A1* | 8/2002 | Sette et al. ................. | 424/93.21 |
| 2006/0165719 A1* | 7/2006 | Sette et al. ................. | 424/191.1 |
| 2008/0248060 A1* | 10/2008 | Bruder et al. ............. | 424/199.1 |
| 2011/0206714 A1* | 8/2011 | Shafferman et al. ...... | 424/191.1 |

* cited by examiner

*Primary Examiner* — Rodney P Swartz
(74) *Attorney, Agent, or Firm* — Albert M. Churilla; Diane P. Tso; Ning Yang

(57) ABSTRACT

The invention relates to a recombinant polypeptide construct comprising epitopes from *Plasmodium falciparum* protein circumsporozoite protein (CSP). The epitopes contain HLA class I binding motifs and stimulate an anti-malaria $CD8^+$ T-cell response. The polypeptides can be incorporated into immunogenic formulations against malaria. Additionally, the antigens are useful for facilitating evaluation of immunogenicity of candidate malaria vaccines.

13 Claims, No Drawings

SEQUENCE LISTING

```
<160> NUMBER OF SEQ ID NOS: 63

<210> SEQ ID NO 1
<211> LENGTH: 10
<212> TYPE: PRT
<213> ORGANISM: Plasmodium falciparum

<400> SEQUENCE: 1

Phe Leu Phe Val Glu Ala Leu Phe Gln Glu
1               5                   10

<210> SEQ ID NO 2
<211> LENGTH: 9
```

```
<212> TYPE: PRT
<213> ORGANISM: Plasmodium falciparum

<400> SEQUENCE: 2

Phe Leu Phe Val Glu Ala Leu Phe Gln
1               5

<210> SEQ ID NO 3
<211> LENGTH: 9
<212> TYPE: PRT
<213> ORGANISM: Plasmodium falciparum

<400> SEQUENCE: 3

Phe Val Glu Ala Leu Phe Gln Glu Tyr
1               5

<210> SEQ ID NO 4
<211> LENGTH: 10
<212> TYPE: PRT
<213> ORGANISM: Plasmodium falciparum

<400> SEQUENCE: 4

Leu Phe Val Glu Ala Leu Phe Gln Glu Tyr
1               5                   10

<210> SEQ ID NO 5
<211> LENGTH: 10
<212> TYPE: PRT
<213> ORGANISM: Plasmodium falciparum

<400> SEQUENCE: 5

Ser Val Phe Asn Val Val Asn Ser Ser Ile
1               5                   10

<210> SEQ ID NO 6
<211> LENGTH: 9
<212> TYPE: PRT
<213> ORGANISM: Plasmodium falciparum

<400> SEQUENCE: 6

Val Phe Asn Val Val Asn Ser Ile Ile
1               5

<210> SEQ ID NO 7
<211> LENGTH: 9
<212> TYPE: PRT
<213> ORGANISM: Plasmodium falciparum

<400> SEQUENCE: 7

Leu Ile Met Val Leu Ser Phe Leu Phe
1               5

<210> SEQ ID NO 8
<211> LENGTH: 9
<212> TYPE: PRT
<213> ORGANISM: Plasmodium falciparum

<400> SEQUENCE: 8

Ala Ile Leu Ser Val Ser Ser Phe Leu
1               5

<210> SEQ ID NO 9
<211> LENGTH: 10
<212> TYPE: PRT
<213> ORGANISM: Plasmodium falciparum
```

```
<400> SEQUENCE: 9

Ser Val Ser Ser Phe Leu Phe Val Glu Ala
1               5                   10

<210> SEQ ID NO 10
<211> LENGTH: 9
<212> TYPE: PRT
<213> ORGANISM: Plasmodium falciparum

<400> SEQUENCE: 10

Ser Phe Leu Phe Val Glu Ala Leu Phe
1               5

<210> SEQ ID NO 11
<211> LENGTH: 9
<212> TYPE: PRT
<213> ORGANISM: Plasmodium falciparum

<400> SEQUENCE: 11

Ile Met Val Leu Ser Phe Leu Phe Leu
1               5

<210> SEQ ID NO 12
<211> LENGTH: 15
<212> TYPE: PRT
<213> ORGANISM: Plasmodium falciparum

<400> SEQUENCE: 12

Ser Val Ser Ser Phe Leu Phe Val Glu Ala Leu Phe Gln Glu Tyr
1               5                   10                  15

<210> SEQ ID NO 13
<211> LENGTH: 15
<212> TYPE: PRT
<213> ORGANISM: Plasmodium falciparum

<400> SEQUENCE: 13

Ser Val Ser Ser Phe Leu Phe Val Glu Ala Leu Phe Gln Glu Tyr
1               5                   10                  15

<210> SEQ ID NO 14
<211> LENGTH: 15
<212> TYPE: PRT
<213> ORGANISM: Plasmodium falciparum

<400> SEQUENCE: 14

Ser Val Ser Ser Phe Leu Phe Val Glu Ala Leu Phe Gln Glu Tyr
1               5                   10                  15

<210> SEQ ID NO 15
<211> LENGTH: 14
<212> TYPE: PRT
<213> ORGANISM: Plasmodium falciparum

<400> SEQUENCE: 15

Leu Phe Val Glu Ala Leu Phe Gln Glu Tyr Gln Cys Tyr Gly
1               5                   10

<210> SEQ ID NO 16
<211> LENGTH: 15
<212> TYPE: PRT
<213> ORGANISM: Plasmodium falciparum

<400> SEQUENCE: 16
```

```
Phe Leu Phe Val Glu Ala Leu Phe Gln Glu Tyr Gln Cys Tyr Gly
1               5                   10                  15

<210> SEQ ID NO 17
<211> LENGTH: 15
<212> TYPE: PRT
<213> ORGANISM: Plasmodium falciparum

<400> SEQUENCE: 17

Phe Leu Phe Val Glu Ala Leu Phe Gln Glu Tyr Gln Cys Tyr Gly
1               5                   10                  15

<210> SEQ ID NO 18
<211> LENGTH: 15
<212> TYPE: PRT
<213> ORGANISM: Plasmodium falciparum

<400> SEQUENCE: 18

Phe Leu Phe Val Glu Ala Leu Phe Gln Glu Tyr Gln Cys Tyr Gly
1               5                   10                  15

<210> SEQ ID NO 19
<211> LENGTH: 15
<212> TYPE: PRT
<213> ORGANISM: Plasmodium falciparum

<400> SEQUENCE: 19

Glu Ala Leu Phe Gln Glu Tyr Gln Cys Tyr Gly Ser Ser Ser Asn
1               5                   10                  15

<210> SEQ ID NO 20
<211> LENGTH: 15
<212> TYPE: PRT
<213> ORGANISM: Plasmodium falciparum

<400> SEQUENCE: 20

Gln Glu Tyr Gln Cys Tyr Gly Ser Ser Ser Asn Thr Arg Val Leu
1               5                   10                  15

<210> SEQ ID NO 21
<211> LENGTH: 15
<212> TYPE: PRT
<213> ORGANISM: Plasmodium falciparum

<400> SEQUENCE: 21

Glu Leu Asn Tyr Asp Asn Ala Gly Thr Asn Leu Tyr Asn Glu Leu
1               5                   10                  15

<210> SEQ ID NO 22
<211> LENGTH: 15
<212> TYPE: PRT
<213> ORGANISM: Plasmodium falciparum

<400> SEQUENCE: 22

Thr Asn Leu Tyr Asn Glu Leu Glu Met Asn Tyr Tyr Gly Lys Gln
1               5                   10                  15

<210> SEQ ID NO 23
<211> LENGTH: 15
<212> TYPE: PRT
<213> ORGANISM: Plasmodium falciparum

<400> SEQUENCE: 23

Thr Asn Leu Tyr Asn Glu Leu Glu Met Asn Tyr Tyr Gly Lys Gln
```

-continued

```
1               5                   10                  15

<210> SEQ ID NO 24
<211> LENGTH: 15
<212> TYPE: PRT
<213> ORGANISM: Plasmodium falciparum

<400> SEQUENCE: 24

Asn Glu Leu Glu Met Asn Tyr Tyr Gly Lys Gln Glu Asn Trp Tyr
1               5                   10                  15

<210> SEQ ID NO 25
<211> LENGTH: 15
<212> TYPE: PRT
<213> ORGANISM: Plasmodium falciparum

<400> SEQUENCE: 25

Asn Glu Leu Glu Met Asn Tyr Tyr Gly Lys Gln Glu Asn Trp Tyr
1               5                   10                  15

<210> SEQ ID NO 26
<211> LENGTH: 15
<212> TYPE: PRT
<213> ORGANISM: Plasmodium falciparum

<400> SEQUENCE: 26

Asp Lys His Ile Lys Glu Tyr Leu Asn Lys Ile Gln Asn Ser Leu
1               5                   10                  15

<210> SEQ ID NO 27
<211> LENGTH: 15
<212> TYPE: PRT
<213> ORGANISM: Plasmodium falciparum

<400> SEQUENCE: 27

Lys Glu Tyr Leu Asn Lys Ile Gln Asn Ser Leu Ser Thr Glu Trp
1               5                   10                  15

<210> SEQ ID NO 28
<211> LENGTH: 15
<212> TYPE: PRT
<213> ORGANISM: Plasmodium falciparum

<400> SEQUENCE: 28

Lys Glu Tyr Leu Asn Lys Ile Gln Asn Ser Leu Ser Thr Glu Trp
1               5                   10                  15

<210> SEQ ID NO 29
<211> LENGTH: 15
<212> TYPE: PRT
<213> ORGANISM: Plasmodium falciparum

<400> SEQUENCE: 29

Lys Glu Tyr Leu Asn Lys Ile Gln Asn Ser Leu Ser Thr Glu Trp
1               5                   10                  15

<210> SEQ ID NO 30
<211> LENGTH: 15
<212> TYPE: PRT
<213> ORGANISM: Plasmodium falciparum

<400> SEQUENCE: 30

Glu Lys Lys Ile Cys Lys Met Glu Lys Cys Ser Ser Val Phe Asn
1               5                   10                  15
```

<210> SEQ ID NO 31
<211> LENGTH: 15
<212> TYPE: PRT
<213> ORGANISM: Plasmodium falciparum

<400> SEQUENCE: 31

Lys Cys Ser Ser Val Phe Asn Val Val Asn Ser Ser Ile Gly Leu
1               5                   10                  15

<210> SEQ ID NO 32
<211> LENGTH: 15
<212> TYPE: PRT
<213> ORGANISM: Plasmodium falciparum

<400> SEQUENCE: 32

Val Phe Asn Val Val Asn Ser Ser Ile Gly Leu Ile Met Val Leu
1               5                   10                  15

<210> SEQ ID NO 33
<211> LENGTH: 15
<212> TYPE: PRT
<213> ORGANISM: Plasmodium falciparum

<400> SEQUENCE: 33

Val Phe Asn Val Val Asn Ser Ser Ile Gly Leu Ile Met Val Leu
1               5                   10                  15

<210> SEQ ID NO 34
<211> LENGTH: 15
<212> TYPE: PRT
<213> ORGANISM: Plasmodium falciparum

<400> SEQUENCE: 34

Val Asn Ser Ser Ile Gly Leu Ile Met Val Leu Ser Phe Leu Phe
1               5                   10                  15

<210> SEQ ID NO 35
<211> LENGTH: 15
<212> TYPE: PRT
<213> ORGANISM: Plasmodium falciparum

<400> SEQUENCE: 35

Ser Ser Ile Gly Leu Ile Met Val Leu Ser Phe Leu Phe Leu Asn
1               5                   10                  15

<210> SEQ ID NO 36
<211> LENGTH: 15
<212> TYPE: PRT
<213> ORGANISM: Plasmodium falciparum

<400> SEQUENCE: 36

Ser Ser Ile Gly Leu Ile Met Val Leu Ser Phe Leu Phe Leu Asn
1               5                   10                  15

<210> SEQ ID NO 37
<211> LENGTH: 15
<212> TYPE: PRT
<213> ORGANISM: Plasmodium falciparum

<400> SEQUENCE: 37

Ser Ser Ile Gly Leu Ile Met Val Leu Ser Phe Leu Phe Leu Asn
1               5                   10                  15

<210> SEQ ID NO 38

```
<211> LENGTH: 15
<212> TYPE: PRT
<213> ORGANISM: Plasmodium falciparum

<400> SEQUENCE: 38

Ser Val Ser Ser Phe Leu Phe Val Glu Ala Leu Phe Gln Glu Tyr
1               5                   10                  15

<210> SEQ ID NO 39
<211> LENGTH: 15
<212> TYPE: PRT
<213> ORGANISM: Plasmodium falciparum

<400> SEQUENCE: 39

Ser Val Ser Ser Phe Leu Phe Val Glu Ala Leu Phe Gln Glu Tyr
1               5                   10                  15

<210> SEQ ID NO 40
<211> LENGTH: 15
<212> TYPE: PRT
<213> ORGANISM: Plasmodium falciparum

<400> SEQUENCE: 40

Ser Val Ser Ser Phe Leu Phe Val Glu Ala Leu Phe Gln Glu Tyr
1               5                   10                  15

<210> SEQ ID NO 41
<211> LENGTH: 15
<212> TYPE: PRT
<213> ORGANISM: Plasmodium falciparum

<400> SEQUENCE: 41

Phe Leu Phe Val Glu Ala Leu Phe Gln Glu Tyr Gln Cys Tyr Gly
1               5                   10                  15

<210> SEQ ID NO 42
<211> LENGTH: 15
<212> TYPE: PRT
<213> ORGANISM: Plasmodium falciparum

<400> SEQUENCE: 42

Phe Leu Phe Val Glu Ala Leu Phe Gln Glu Tyr Gln Cys Tyr Gly
1               5                   10                  15

<210> SEQ ID NO 43
<211> LENGTH: 15
<212> TYPE: PRT
<213> ORGANISM: Plasmodium falciparum

<400> SEQUENCE: 43

Phe Leu Phe Val Glu Ala Leu Phe Gln Glu Tyr Gln Cys Tyr Gly
1               5                   10                  15

<210> SEQ ID NO 44
<211> LENGTH: 15
<212> TYPE: PRT
<213> ORGANISM: Plasmodium falciparum

<400> SEQUENCE: 44

Glu Ala Leu Phe Gln Glu Tyr Gln Cys Tyr Gly Ser Ser Ser Asn
1               5                   10                  15

<210> SEQ ID NO 45
<211> LENGTH: 15
<212> TYPE: PRT
```

-continued

<213> ORGANISM: Plasmodium falciparum

<400> SEQUENCE: 45

Gln Glu Tyr Gln Cys Tyr Gly Ser Ser Ser Asn Thr Arg Val Leu
1               5                   10                  15

<210> SEQ ID NO 46
<211> LENGTH: 15
<212> TYPE: PRT
<213> ORGANISM: Plasmodium falciparum

<400> SEQUENCE: 46

Ser Ser Asn Thr Arg Val Leu Asn Glu Leu Asn Tyr Asp Asn Ala
1               5                   10                  15

<210> SEQ ID NO 47
<211> LENGTH: 15
<212> TYPE: PRT
<213> ORGANISM: Plasmodium falciparum

<400> SEQUENCE: 47

Glu Leu Asn Tyr Asp Asn Ala Gly Thr Asn Leu Tyr Asn Glu Leu
1               5                   10                  15

<210> SEQ ID NO 48
<211> LENGTH: 15
<212> TYPE: PRT
<213> ORGANISM: Plasmodium falciparum

<400> SEQUENCE: 48

Thr Asn Leu Tyr Asn Glu Leu Glu Met Asn Tyr Tyr Gly Lys Gln
1               5                   10                  15

<210> SEQ ID NO 49
<211> LENGTH: 15
<212> TYPE: PRT
<213> ORGANISM: Plasmodium falciparum

<400> SEQUENCE: 49

Thr Asn Leu Tyr Asn Glu Leu Glu Met Asn Tyr Tyr Gly Lys Gln
1               5                   10                  15

<210> SEQ ID NO 50
<211> LENGTH: 15
<212> TYPE: PRT
<213> ORGANISM: Plasmodium falciparum

<400> SEQUENCE: 50

Asn Glu Leu Glu Met Asn Tyr Tyr Gly Lys Gln Glu Asn Trp Tyr
1               5                   10                  15

<210> SEQ ID NO 51
<211> LENGTH: 15
<212> TYPE: PRT
<213> ORGANISM: Plasmodium falciparum

<400> SEQUENCE: 51

Asp Lys His Ile Lys Glu Tyr Leu Asn Lys Ile Gln Asn Ser Leu
1               5                   10                  15

<210> SEQ ID NO 52
<211> LENGTH: 15
<212> TYPE: PRT
<213> ORGANISM: Plasmodium falciparum

<400> SEQUENCE: 52

Lys Glu Tyr Leu Asn Lys Ile Gln Asn Ser Leu Ser Thr Glu Trp
1               5                   10                  15

<210> SEQ ID NO 53
<211> LENGTH: 15
<212> TYPE: PRT
<213> ORGANISM: Plasmodium falciparum

<400> SEQUENCE: 53

Lys Glu Tyr Leu Asn Lys Ile Gln Asn Ser Leu Ser Thr Glu Trp
1               5                   10                  15

<210> SEQ ID NO 54
<211> LENGTH: 15
<212> TYPE: PRT
<213> ORGANISM: Plasmodium falciparum

<400> SEQUENCE: 54

Lys Glu Tyr Leu Asn Lys Ile Gln Asn Ser Leu Ser Thr Glu Trp
1               5                   10                  15

<210> SEQ ID NO 55
<211> LENGTH: 14
<212> TYPE: PRT
<213> ORGANISM: Plasmodium falciparum

<400> SEQUENCE: 55

Lys Lys Ile Cys Lys Met Glu Lys Cys Ser Ser Val Phe Asn
1               5                   10

<210> SEQ ID NO 56
<211> LENGTH: 15
<212> TYPE: PRT
<213> ORGANISM: Plasmodium falciparum

<400> SEQUENCE: 56

Lys Cys Ser Ser Val Phe Asn Val Val Asn Ser Ser Ile Gly Leu
1               5                   10                  15

<210> SEQ ID NO 57
<211> LENGTH: 15
<212> TYPE: PRT
<213> ORGANISM: Plasmodium falciparum

<400> SEQUENCE: 57

Val Phe Asn Val Val Asn Ser Ser Ile Gly Leu Ile Met Val Leu
1               5                   10                  15

<210> SEQ ID NO 58
<211> LENGTH: 15
<212> TYPE: PRT
<213> ORGANISM: Plasmodium falciparum

<400> SEQUENCE: 58

Val Phe Asn Val Val Asn Ser Ser Ile Gly Leu Ile Met Val Leu
1               5                   10                  15

<210> SEQ ID NO 59
<211> LENGTH: 15
<212> TYPE: PRT
<213> ORGANISM: Plasmodium falciparum

<400> SEQUENCE: 59

```
Val Asn Ser Ser Ile Gly Leu Ile Met Val Leu Ser Phe Leu Phe
1               5                   10                  15

<210> SEQ ID NO 60
<211> LENGTH: 15
<212> TYPE: PRT
<213> ORGANISM: Plasmodium falciparum

<400> SEQUENCE: 60

Ser Ser Ile Gly Leu Ile Met Val Leu Ser Phe Leu Phe Leu Asn
1               5                   10                  15

<210> SEQ ID NO 61
<211> LENGTH: 15
<212> TYPE: PRT
<213> ORGANISM: Plasmodium falciparum

<400> SEQUENCE: 61

Ser Ser Ile Gly Leu Ile Met Val Leu Ser Phe Leu Phe Leu Asn
1               5                   10                  15

<210> SEQ ID NO 62
<211> LENGTH: 15
<212> TYPE: PRT
<213> ORGANISM: Plasmodium falciparum

<400> SEQUENCE: 62

Ser Ser Ile Gly Leu Ile Met Val Leu Ser Phe Leu Phe Leu Asn
1               5                   10                  15

<210> SEQ ID NO 63
<211> LENGTH: 10
<212> TYPE: PRT
<213> ORGANISM: Plasmodium falciparum

<400> SEQUENCE: 63

Leu Ile Met Val Leu Ser Phe Leu Phe Leu
1               5                   10
```

RECOMBINANT POLYPEPTIDE CONSTRUCT COMPRISING *PLASMODIUM FALCIPARUM* CIRCUMSPOROZOITE PROTEIN HLA CLASS I RESTRICTED T-CELL EPITOPES

CROSS-REFERENCES TO RELATED APPLICATIONS

This application claims priority to U.S. Provisional application 61/724,374 filed Nov. 9, 2012.

BACKGROUND OF INVENTION

Field of Invention

The inventive subject matter relates to *Plasmodium falciparum* circumsporozoite protein (CSP) polypeptides containing HLA-restricted CD8$^+$ T-cell epitopes. The inventive polypeptides or epitopes can be utilized in assays to evaluate candidate vaccines to malaria. Additionally, the polypeptides can be incorporated into vaccine formulations against *P. falciparum*.

Background Art

Malaria is caused by the vector borne organism *Plasmodium* spp. The parasite has a complex lifecycle involving stage specific expression of proteins. These proteins can be expressed at different stages or be specific to stages. Malaria is an extremely important disease, with over 3 billion people living in malaria endemic areas. Over 1 million deaths are attributable to malaria per year. The emergence of drug resistant strains has compounded the problem of treating the disease. Unfortunately, no FDA-approved vaccine exists.

The entire genomic sequence of *P. falciparum* has been sequenced (Bowman et al., Nature, 400: 532-538 (1999); Gardner, et al., Nature, 419: 498-511 (2002)). The rodent malaria parasite, *P. yoelii* has also been sequenced (Carlton et al., Nature, 419: 512-519 (2002)). Despite this, however, the development of efficacious anti-malaria vaccines has been severely hampered by the paucity of promising antigens. As such, no FDA-approved vaccine to this agent exists.

Sterile protective immunity to malaria induced by experimental immunization with irradiated sporozoites is thought to be mediated by CD4+ and CD8+ T cells directed against malaria antigens expressed on the surface of infected hepatocytes and perhaps anti-sporozoite antibodies (Agnandji, et al., N. Engl. J. Med., 365: 1863-75 (2011)). Naturally acquired anti-malarial immunity is mediated primarily by antibodies to blood-stage parasites with T cell responses possibly providing a contribution. Both CD4+ and CD8+ T cells are needed for optimal effector cell functions. Furthermore, the development of immunological memory (Beeson, et al., Trends Parasitol 24: 578-584 (2008)) and T cell responses is known to be genetically restricted.

The circumsporozoite protein (CSP) is the main antigenic component of the RTS,S vaccine that has demonstrated ≈50% efficacy in Phase 3 trials in Sub-Saharan Africa (Agnandji, et al., N. Engl. J. Med., 365: 1863-75 (2011)). While RTS,S induces anti-CSP antibodies and CD4+ T cell responses thought to be associated with protection (Moorthy and ballou, Malar J., 8: 312 (2009)), CD8+ T cell responses to CSP have not been consistently demonstrated in RTS,S vaccinated individuals (Moorthy and ballou, Malar J., 8: 312 (2009)), which may limit its ability to target the liver stage of *Plasmodium*. It has been suggested that vaccine strategies promoting the induction of CD8+ T cell responses to RTS,S, such as priming with adenovirus vectored vaccines, might improve protection.

SUMMARY OF THE INVENTION

The invention relates to polypeptides containing HLA-restricted CD8+ T-cell epitopes from the *P. falciparum* protein CSP. In one embodiment, one or more polypeptides can be included in immunogenic composition against malaria. In this embodiment, one or more proteins can be produced by first inserting the DNA encoding the proteins in suitable expression systems. The expressed and purified proteins can then be administered in one or multiple doses to a mammal, such as humans. In this embodiment, the purified proteins can be expressed individually or DNA encoding specific proteins can be recombinantly associated to form a single immunogenic composition. These immunogenic compositions can then be administered in one or multiple doses to induce an immunogenic response.

In an alternative embodiment, DNA encoding the proteins can be inserted into suitable vector expression systems. These include, for example, adenoviral based systems, such as in Bruder, et al (patent application publication number US 20080248060, published Oct. 9, 2008) or a DNA plasmid system.

In order to develop anti-malaria vaccines that stimulate an enhanced cell mediated response, it is important for the vaccine to contain appropriate CD4$^+$ and CD8$^+$ T-cell epitopes. CD8+ T cell responses that produce IFN-γ and multifunctional responses (i.e., produce more than 2 cytokines) have been associated with protection in other diseases (Darrah, et al., Nat Med., 13: 843-50 (2007); Seder, et al., Nat Rev Immunol., 8: 247-58 (2008); Lindenstrom, et al., J. Immunol., 182: 8047-55 (2009); Valor, et al., Vaccine, 26: 2738-45 (2008); Barisal, et al., J. Virol., 82: 6458-69 (2008); Walther, et al., Infect. Immun., 74: 2706-16 (2006); Karanam, et al., Vaccine 27: 1040-9 (2009)). For this reason, it is important develop immunogenic candidates that contain T-cell epitopes.

In a preferred embodiment, polypeptides of specific regions of the *P. falciparum* CSP were identified and isolated, which contain CD8$^+$ T cell epitopes. Because of the importance of CD8$^+$ T-cells in conferring immunity to malaria, these polypeptides are useful as components of immunogenic compositions against malaria.

There are many hundreds of HLA A and B alleles that can be classified into 12 Class I super-types that cover most of the known HLA-A and HLA-B polymorphisms, permitting identification of potential peptide binding motifs that should recognize the super-types (Sette, A. and J. Sidney, Immunogenetics 50: 201-12 (1999)). Algorithms have been developed to aid prediction of peptide sequences that bind to CD4$^+$ or CD8$^+$ T cells (Gowthaman, U. and J. N. Agrewala, Expert Rev Proteomics 6: 527-37 (2009); Tian, et al., Amino Acids 36: 535-54 (2009); Hattotuwagama, et al., Methods Mol Biol. 409: 227-45 (2007)).

In a preferred embodiment, is an immunogenic composition comprising one or more of 11 putative predicted minimal epitopes that are identified of which six were confirmed as recalling CD8+ T cell responses. These are restricted by five HLA-A and two HLA B supertypes that together are expressed by 99.5% of Caucasians and 98.1% African Americans Sette) and Sidney, Immunogenetics, 50: 201-12 (1999)). In addition, CSP class I epitopes have been shown to be degenerate and are recognized by multiple HLA alleles (Doolan, et al., Immunity, 7: 97-112 (1997)), and we found similar degeneracy in this study. Therefore it is likely that these adenovectored CSP vaccines will elicit CD8+ T cell responses in a genetically diverse population. The CSP epitopes identified herein can form part of an epitope based vaccine against malaria.

DETAILED DESCRIPTION OF PREFERRED EMBODIMENTS

The following terms are defined: Antigen is a chemical moiety containing at least one epitope capable of stimulating or reacting with immune products, such as antibody or T-cells; T-cell Epitope is defined in this application as a minimal polypeptide region capable of stimulating a T-cell response. As used herein, the term "mer", in conjunction with a number, such as 15-mer, refers to the length of a polypeptide in numbers of amino acids.

As used in this application, an epitope is typically 8 to 10 amino acids; CSP refers to circumsporozoite protein, which is a protein expressed by *Plasmodium falciparum*; an HLA motif is an amino acid sequence associated with binding to HLA molecules and can be associated with T-cell recognition of antigen in an HLA-restricted fashion; the term recombinant polypeptide, recombinant polypeptide construct, or recombinant protein, as used herein, refers to polypeptides or proteins produced by recombinant DNA techniques, i.e., produced from cells transformed by an exogenous DNA construct encoding the desired polypeptide or the desired protein or produced by other synthetic means. The term recombinant construct refers to the DNA encoding the recombinant polypeptide, recombinant polypeptide construct or recombinant protein: an Immunogenic composition refers to a chemical, compound or formulation that, once administered, will elicit an immune response; a vaccine is an immunogenic composition used to induce protective immunity; a DNA expression system is a molecular system containing plasmid or closed loop DNA containing elements for expressing an inserted DNA sequence as polypeptide; HLA refers to human leukocyte antigens; a viral expression system is any viral based system, including viral-like particles or viral replicons, containing elements for expressing an inserted DNA sequence as a polypeptide.

In some embodiments, the claimed *P. falciparum* epitopes include derivatives with 80% or more amino acid sequence identity to the claimed sequences. In this context, the term identity refers to two or more sequences or subsequences that are the same or have a specified percentage of amino acid residues that are the same, when aligned for maximum correspondence. Where sequences differ in conservative substitutions, i.e., substitution of residues with identical properties, the percent sequence identity may be adjusted upwards to correct for the conservative nature of the substitution.

CD4$^+$ and CD8$^+$, HLA-restricted T cells are needed for optimal effector cell functions. Therefore it is necessary to ensure that malaria vaccines contain appropriate HLA-restricted CD4+ and CD8+ T cell epitopes that are recognized by as wide a population as possible. Secondly, identification of such epitopes that can be combined into a single pool for stimulating PBMC has the potential to facilitate the determination of immunogenicity of candidate malaria vaccines where cell numbers can are limited.

In order to develop anti-malaria vaccines that stimulate an enhanced cell mediated response, it is important to map the HLA-restricted T-cell epitopes of potentially important malarial antigens, such as CSP. CD8$^+$ T cell responses that produce IFN-γ and multifunctional responses (i.e., produce more than 2 cytokines) have been associated with protection in other diseases (Darrah, et al., Nat Med., 13: 843-50 (2007); Seder, et al., Nat Rev Immunol., 8: 247-58 (2008); Lindenstrom, et al., J. Immunol., 182: 8047-55 (2009); Valor, et al., Vaccine, 26: 2738-45 (2008); Bansal, et al., J. Virol., 82: 6458-69 (2008); Walther, et al., Infect. Immun., 74: 2706-16 (2006); Karanam, et al., Vaccine 27: 1040-9 (2009)). For this reason, it is important development of immunogenic candidates containing T-cell epitopes, especially, CD8$^+$ epitopes.

In a preferred embodiment, polypeptides of the *Plasmodium falciparum* protein, CSP regions were identified and isolated that contain CD8$^+$ T-cell epitopes. One or more of these polypeptides from these regions can be used in immunogenic compositions against malaria.

Hundreds of HLA-A and -B alleles exist and that can be classified into 12 Class I super-types that cover most of the known HLA-A and HLA-B polymorphisms, allowing identification of a potential peptide binding motifs that should recognize the super-types (Sette, A. and J. Sidney, Immunogenetics 50: 201-12 (1999)). Algorithms have been developed to aid prediction of peptide sequences that bind to CD4+ or CD8+ T cells (Gowthaman, U. and J. N. Agrewala, Expert Rev Proteomics 6: 527-37 (2009); Tian, et al., Amino Acids 36: 535-54 (2009); Hattotuwagama, et al., Methods Mol Biol. 409: 227-45 (2007)).

The computerized algorithm NetMHC (Nielsen, et al., Protein Sci., 12: 1007-1017 (2003)) was used to predict the binding affinities of 8-10 mer peptides contained within overlapping 15 mer peptides of CSP.

CSP has three distinct regions: the N-terminal region containing the conserved region I sequence; the central repeat region; and the C-terminal region containing the thrombospondin-like type I repeat (TSR) that functions in hepatocyte invasion (Coppi, et al, J. Exp. Med. 208: 341-56 (2011)) RTS,S contains part of the central repeat and the C-terminal region, but recent studies have demonstrated that antibodies associated with protection also recognize epitopes in the N-terminal region (Bongfen, et al., Vaccine, 27: 328-35 (2009)), not present in RTS,S. The regions of CSP that might lead to effective targeting by CD8+ T cells have not yet been functionally defined.

Therefore, it was important to next identify class I-restricted epitopes within CSP. Previous studies using peptides have identified a series of DR-restricted (Doolan, et al., J. Immunol., 165: 1123-37 (2000); Lockyer, et al., Mol. Biochem. Parasitol, 37: 275-80 (1989); Jalloh, et al., Malar J., 8: 120 (2009); Nardin, et al., J. Immunol., 166: 481-9 (2001); Calvo-Calle, et al., J. Immunol. 159: 1362-73 (1997); Kumar, et al., Nature, 344: 258-60 (1988); Good, et al., PNAS (USA), 85: 1199-203 (1988)) and CD8+-restricted epitopes in the N- and C-terminal regions of CSP (Hill, et al., Nature, 360: 434-9 (1992); Doolan, et al., Immunity, 7: 97-112 (1997); Blum-Tirouvanziam, et al., J. Immunol., 154: 3922-31 (1995); Aidoo, et al., Lancet, 345: 1003-7 (1995); Wang, et al., Science, 282: 476-80 (1998)). Class II-restricted epitopes are promiscuous, binding to multiple alleles (Panina-Bordignon, et al., Eur. J. Immunol., 19: 2237-42 (1989)), including epitopes in malaria antigens, such as the DR-restricted epitopes in CSP (Doolan, et al., J. Immunol., 165: 1123-37 (2000). Promiscuity in class I-restricted epitopes has also been described for malaria antigens including CSP (Doolan, et al., Immunity, 7: 97-112 (1997)) and has been extended to include epitopes from other organisms (Frahm, et al., J. Virol, 78: 2187-200 (2004); Frahm, et al., Eur. J. Immunol., 37: 2419-33 (2007)).

Similarities in binding motifs among HLA class I alleles has allowed clustering into nine supertypes (Sidney, et al., J. Immunol, 154: 247-59 (1995); Lund, et al., Immunogenetics, 55: 797-810 (2004); Sette and Sidney, Immunogenetics, 50: 201-12 (1999)). Based on algorithms that predict binding to MHC molecules, measured as 50% inhibitory concentration ($IC_{50}$) values expressed in nM (Sette, et al., J. Immunol., 153: 5586-92 (1994)), a meta-analysis using an affinity cut off of 500 nM predicted that 52% of a panel P. falciparum peptides bound to HLA A*0201 (Doolan, et al., PNAS (USA), 100: 9952-7 (2003)), and led to the development of publically available algorithms that are specific for class I and class II types (Doolan, et al., PNAS (USA), 100: 9952-7 (2003)). The outcomes of these and similar studies has led to the establishment of the Immune Epitope Database and Analysis Resource (IEDB) that contains data and analytical tools from a wide range of organisms including malaria (Vaughn, et al., Parasite Immunolo., 31: 78-97 (2009)). Recently, analysis of the IEDB data base suggests that >50% of HLA class I-restricted ligands bind to two or more HLA molecules often spanning different supertypes (Rao, et al., Immunogenetics, 63: 691-701 (2011). Since CD8+ T cell responses appear crucial in targeting the intracellular hepatic stage, we decided to further characterize CD8+ T cell responses in these immunized volunteers by mapping CSP class I-restricted epitopes.

Frozen peripheral blood mononuclear cells (PBMC) collected from volunteers immunized with either a mixture of two adenovectors encoding CSP and AMA1 respectively (AD-CA) (Sedegah, et al., PLoS One, 6: e24586 (2011)) or with the adenovectored encoding CSP given alone (Ad-C) (Tamminga, et al., PLoS One, 6: e25868 (2011)) were selected for mapping the CSP CD8+ epitopes. We have previously used a combination of peptide-based mapping and the computer-based algorithm NetMHC (Nielsen, et al., Protein Sci., 12: 1007-17 (2003)) to identify class I epitopes in AMA1 (Sedegah, et al., Malar, J., 9: 241 (2011)), and adopted a similar approach here.

Peptide pools containing overlapping 15mer peptides that showed positive responses in ELISpot assays with volunteers immunized with these CSP vaccines were analyzed using NetMHC to predict putative CD8+-restricted epitopes within active 15mers. A subset of the predicted epitopes was synthesized, and ELISpot assays were used to confirm recall responses by stimulating PBMC from the immunized volunteers with these minimal epitopes. CD8+ T cell responses were demonstrated by flow cytometry and CD8+ T cell-dependence by ELISpot depletion studies. PBMCs were sufficient to confirm eleven of the novel CD8+ T cell dependent epitopes, of which six were from the N-terminal and five were from the C-terminal regions. Finally, we identified evidence to support the concept of class I-restricted epitope promiscuity.

The NMRC-M3V-Ad-PfCA vaccine used in this study is a combination of two recombinant human adenovirus serotype 5 constructs (Ad5), one expressing full length P. falciparum CSP (minus 16 repeats and insertion of 23 amino acids derived from the 3'-noncoding bovine growth hormone polyadenylation sequence at the C-terminus) and the other expressing full length P. falciparum AMA1. This vaccine was evaluated in three different clinical trials. In the first trial, six volunteers were immunized with $2\times10^{10}$ pu of both adenovectors (Ad-CA) as a single dose into the deltoid muscle by needle injection, and six different volunteers received a five-fold higher dose (Sedegah, et al., PLoS One, 6: e24586 (2011)). In the second trial, 11 volunteers were immunized twice with $1\times10^{10}$ pu of the Ad5 P. falciparum CSP vaccine alone (Ad-C) with a 16 week interval; these volunteers were challenged by bite of P. falciparum-infected mosquitoes 28 days after the second vaccine dose (Tamminga, et al., PLoS One, 6: e25868 (2011)). In the third trial, 17 volunteers were immunized once with $2\times10^{10}$ pu of both adenovectors (Ad-CA) and were challenged by bite of P. falciparum-infected mosquitoes. None of the volunteers in the two challenge studies was sterilely protected against malaria. However, the vaccines were strongly immunogenic for CD4+ and CD8+ T cell responses. A limited supply of peripheral blood mononuclear cells (PBMC) remaining after the primary analysis of immunogenicity for the various trials were used for epitope mapping.

EXAMPLE 1

HLA Typing

Volunteers were selected who exhibited a strong responses and for whom PBMC were available (Table 1). HLA molecular typing for HLA-A and HLA-B loci using specific oligonucleotide probes to amplify HLA Class I genes, and provided a list of allelic codes from which it was possible to assign each volunteer to an HLA-A or HLA-B allele groups using code lists (Table 1). Each HLA-A or HLA-B allele group was then assigned to HLA A or HLA B supertypes according to published guidelines (Sette, and Sidney, Immunogenetics, 50: 201-12 (1999); Sidney, et al., BMC Immunol., 9: 1 (2008)).

TABLE 1

Volunteer HLA A and B allele groups and supertypes[1]

| Vaccine | Vol. | Trial | HLA A allele groups | HLA B Allele groups | HLA A Supertype | HLA B supertype |
|---|---|---|---|---|---|---|
| Ad-CA | 1 | 1 | A*02:01/A*26:01 | B*18:01/B*44:02 | A02/A01 | B44/B44 |
|  | 2 | 1 | A*01:01/A*02:01 | B*08:01/B*44:02 | A01/A02 | B08/B44 |
|  | 5 | 1 | A*01:01/A*68:02 | B*08:01/B*14:02 | A01/A02 | B08/B27 |
|  | 8 | 1 | A*68:01/A*68:02 | B*14:02/B*48:01 | A03/A02 | B27/B27 |
|  | 12 | 1 | A*30:02/A*68:01 | B*18:01/B*58:02 | A01/A03 | B44/B58 |
|  | 125 | 2 | A*02:01/A*11:01 | B*35:01/B*52:01 | A02/A03 | B07/B62 |
|  | 127 | 2 | A*01:01/A*24:02 | B*08:01/B*44:05 | A01/A24 | B08/B44 |
|  | 156 | 2 | A*03:01/A*29:02 | B*15:03/B*58:02 | A03/A01A24 | B27/B58 |
| Ad-C | 37 | 3 | A*23:01/A*68:02 | B*15:03/B*53:01 | A24/A02 | B27/B07 |
|  | 40 | 3 | A*23:01/A*29:02 | B*52:01/B*53:01 | A24/A01 | B62/B07 |
|  | 41 | 3 | A*02:01/A*31:01 | B*07:02/B*35:01 | A02/A03 | B07/B07 |
|  | 49 | 3 | A*33:01/A*74:01 | B*15:03/B*15:03 | A03/A03 | B27/B27 |
|  | 58 | 3 | A*02:01/A*24:01 | B*08:01/B*38:02 | A02/A24 | B08/B08 |
|  | 61 | 3 | A*02:01/A*02:01 | B*38:01/B*44:02 | A02/A02 | B08/B08 |

TABLE 1-continued

Volunteer HLA A and B allele groups and supertypes[1]

| Vaccine | Vol. | Trial | HLA A allele groups | HLA B Allele groups | HLA A Supertype | HLA B supertype |
|---|---|---|---|---|---|---|
| | 63 | 3 | A*11:01/A*24:03 | B*40:01/B*51:04 | A03/A24 | B44/B07 |
| | 68 | 3 | A*24:02/A*30:01 | B*13:02/B*14:02 | A24/A01A03 | B62/B27 |
| | 69 | 3 | A*30:02/A*34:02 | B*14:02/B*35:01 | A01/A03 | B27/B07 |

[1]The volunteers from whom PBMC were available and were tested are shown. Trial 1 used six volunteers immunized with Ad-CA (reference 5); trial 2 used 17 volunteers immunized with Ad-CA and challenged by bite of *P. falciparum*-infected mosquitoes (reference 6); trial 3 used 11 volunteers immunized with Ad-C and challenged by bite of *P. falciparum*-infected mosquitoes.

In the studies, cryopreserved PBMC were collected 28 days following immunization, when responses peak, were selected. Previous studies have confirmed that recall-T cell responses, as assayed by ELISpot, are detected using cryopreserved PBMCs although such responses are generally of a lower magnitude than fresh cells (Sedegah, et al., Malar J., 9: 241 (2011)).

Sixty-five 15mer peptides overlapping by 11 amino acids and spanning the full length of CSP (3D7 strain), as previously reported (Sedegah, et al., PLoS One 6: e24586 (2011)), were synthesized commercially (Mimotopes, VIC, Australia, >80% purity) and grouped into 9 peptide pools containing three to 14 peptides in each. Four of these pools (Cp1, Cp2, Cp6, and Cp9) containing 26 peptides elicited ELISpot responses among the volunteers who received Ad-CA defined as greater than 33% of the activity of the highest response to one of the pools, and thus were considered immunodominant (Sedegah, et al., PLoS One 6: e24586 (2011)). These 26 peptides were then assayed individually in ELISpot with selected volunteers and 15 individual 15mers had positive ELISpot responses, as defined below. Ten predicted 8-10mer epitopes identified within these 15 15mers were synthesized (Alpha Diagnostics Intl. Inc., San Antonio, Tex., USA >91% purity) and tested for recall responses. The positive control was commercially obtained Class I Peptide Pool Plus (Anaspec, USA). Negative control was media with all supplements but no antigen-specific stimulant.

Throughout the studies, IFN-γ ELISpot assays were conducted as previously described (Sedegah, et al., Malar J., 9: 241 (2011); Wang, et al., PNAS (USA), 98: 10817-22 (2001)). Cryopreserved PBMC were suspended in 100 μL complete medium and stimulated with CSP peptides in 100 μL of complete medium at a final concentration of 10 μg/mL of each peptide tested (Wang, et al., PNAS (USA), 98: 10817-22 (2001)).

Cultures were incubated for 36 hours at 37° C., 5% CO2. Depending on availability of cells, each PBMC sample was assayed in duplicate, triplicate, or quadruplicate and the number of IFN-γ-secreting spot forming cells (sfc) was counted using an automated ELISpot reader (AID, GmbH, Germany). In duplicate assays, all values were used in analysis. For triplicate or quadruplicate assays, outliers were rejected if any single value contributed more than 50% of the standard deviation of the replicates and if its value was three-fold greater or three-fold less than the average of the remaining two (or three) values. The mean number of sfcs obtained in negative control wells was subtracted from the value of each test well from the same sample. Negative counts generated by this background subtraction were converted to zero. The mean number of spots of the test sample was then calculated and expressed as spot forming cells/million (sfc/m). A positive response was defined as a significant difference (p=<0.05) between average of the number of spot forming cells (sfc) in test wells and the average of negative control wells (Student's two tailed t-test), and at least a doubling of sfc in test wells relative to negative control wells, and a difference of at least ten sfc between test and negative control wells (Sedegah, et al., PLoS One, 6: e24586 (2011)).

For characterization of ELISpot IFN-γ-producing cells by T-cell subset depletions PBMC were depleted of T-cell subsets using anti-human CD4+ or anti-CD8+ coated Dynabeads M-450 (Dynal, Great Neck, N.Y.) following the manufacturer's instructions. Mock depletion was done with Dynabeads coated with sheep anti-mouse IgG. Flow cytometry confirmed that T-cell subset depletions were >99% in all experiments. Data are presented as the spot-forming cells/million (sfc/m) and percent decrease or increase in activity after depletion.

Intracellular cytokine staining (ICS) was performed as published previously (Stewart, et al, Infect. Immun., 75: 2283-90 (2007)). Cryopreserved PBMC were thawed, washed, and resuspended at $10 \times 10^6$ cells per mL in complete medium. Peptides were used at 10 μg/mL and costimulatory antibodies anti-CD28 and anti-CD4+9d (BD Bioscience, San Jose, Calif.) were used at 1 μg/mL. Stimulants were added to cells and incubated at 37° C. with 5% $CO_2$ for 2 hours. Cells were stained with anti-CD3, anti-CD4, anti-CD8, anti-IFN-γ, anti-TNFα, and anti-IL2 and the entire available sample was acquired on a BD LSRII using FACSDiVa (BD Bioscience) software. Data were analyzed using FlowJo Software (Treestar, Inc.). The gating strategy involved progressively measuring total cells; viable cells; lymphocytes; T cells; CD4+ or CD8+ populations; and finally a specific cell type expressing a specific cytokine. Results were transferred to Prism (GraphPad) for graphing and statistical analysis. Data for peptides were corrected for media responses. A positive response was greater than the medium controls+3 standard deviations (0.03%).

Having established which 15mer peptides were active in ELISpot, we used NetMHC (Nielson, et al., Protein Sci, 12: 1007-17 (2003)) to predict the MHC class 1 binding affinities of minimal 8-10mer epitopes within the 15mers that matched the HLA alleles expressed by the volunteers used in each assay. NetMHC returns predicted binding affinity scores that approximate the half maximal inhibitory concentration ($IC_{50}$) in nM. Peptides with predicted $IC_{50}$ binding affinities less than 500 nM were considered binders, 500-5000 nM are considered weak binders, >5000 nM is a non-binder (Sette, et al., Mol. Immunol., 31: 813-22 (1994)). We have previously shown that some AMA1 epitopes have predicted $IC_{50}$>500 (Sedegah, et al., Malar J., 9: 241 (2011)), consistent with the previously reported meta-analysis of *Plasmodium* epitopes (Vaughan, et al., Parasite Immunol., 31: 78-97 (2009)).

EXAMPLE 2

ELISpot Activity

Previous studies indicated that four of the nine CSP peptide pools (Cp1, Cp2, Cp6, and Cp9) recalled the highest responses in ELISpot assays with volunteers immunized with Ad-CA or Ad-C vaccines (Sedegah, et al., PLoS One, 6: e24586 (2011); Tamminga, et al., PLoS One, 6: e25868 (2011)). Therefore, the high responding volunteers were evaluated against all the 15mers within each pool they responded to based on PBMC availability. Cp1 contains seven 15mers, labeled Cp1-C1 to Cp1-C7; Cp2 contains eight 15mers, Cp2-C8 to Cp2-C15; Cp6 contains three 15mers, Cp6-C46 to Cp6-C48, and Cp9 contains eight 15mers, Cp9-058 to Cp9-C65. Fifteen of the 26 tested 15mers were positive by ELISpot: four from Cp1, four from Cp2, two from Cp6, and five from Cp9. The results are illustrated in Table 2. As shown in Table 2, some peptides were positive with volunteers immunized with both Ad-CA or Ad-C vaccines (Table 2): Cp1-C3 with v05 (Ad-CA) and v58 and v69 (Ad-C); Cp1-C4 with v01, v05 and v12 (Ad-CA) and v69 (Ad-C); Cp6-C48 with v05 (Ad-CA) and v41 and v58 (Ad-C); and Cp9-C63 with v08 (Ad-CA) and v61 (Ad-C). Although responses varied, it appears that the inclusion of the AMA1 in the Ad-CA vaccine did not interfere with CSP epitope recognition by immune PBMC.

TABLE 2

ELISpot IFN-γ activity of CSP peptide pools and individual 15-mer peptides within these pools[1]

| Pool | Vol. | Vaccine | Pool sfc/m | 15 mer peptide | AA No. | Sequence (SEQ ID NO.) | 15 mer sfc/m |
|---|---|---|---|---|---|---|---|
| Cp1 | 58 | Ad-C | 116 | Cp1-C3 | 9-23 | SVSSFLFVEALFQEY (12) | 29 |
| Cp1 | 05 | Ad-CA | 142 | Cp1-C3 | | SVSSFLFVEALFQEY (13) | 65 |
| Cp1 | 69 | Ad-C | 411 | Cp1-C3 | | SVSSFLFVEALFQEY (14) | 385 |
| Cp1 | 12 | Ad-CA | 64 | Cp1-C4 | 13-27 | FLFVEALFQEYQCYG (15) | 87 |
| Cp1 | 05 | Ad-CA | 142 | Cp1-C4 | | FLFVEALFQEYQCYG (16) | 44 |
| Cp1 | 01 | Ad-CA | 77 | Cp1-C4 | | FLFVEALFQEYQCYG (17) | 48 |
| Cp1 | 69 | Ad-C | 411 | Cp1-C4 | | FLFVEALFQEYQCYG (18) | 368 |
| Cp1 | 58 | Ad-C | 116 | Cp1-05 | 17-31 | EALFQEYQCYGSSSN (19) | 105 |
| Cp1 | 58 | Ad-C | 116 | Cp1-C6 | 21-35 | QEYQCYGSSSNTRVL (20) | 83 |
| Cp2 | 41 | Ad-C | 83 | Cp2-C10 | 37-51 | ELNYDNAGTNLYNEL (21) | 35 |
| Cp2 | 12 | Ad-CA | 331 | Cp2-C12 | 45-59 | TNLYNELEMNYYGKQ (22) | 411 |
| Cp2 | 01 | Ad-CA | 119 | Cp2-C12 | | TNLYNELEMNYYGKQ (23) | 119 |
| Cp2 | 01 | Ad-CA | 119 | Cp2-C13 | 49-63 | NELEMNYYGKQENWY (24) | 116 |
| Cp2 | 12 | Ad-CA | 331 | Cp2-C13 | 49-63 | NELEMNYYGKQENWY (25) | 334 |
| Cp6 | 61 | Ad-C | 53 | Cp6-C47 | 313-327 | DKHIKEYLNKIQNSL (26) | 48 |
| Cp6 | 41 | Ad-C | 95 | Cp6-C48 | 317-331 | KEYLNKIQNSLSTEW (27) | 103 |
| Cp6 | 05 | Ad-CA | 130 | Cp6-C48 | | KEYLNKIQNSLSTEW (28) | 106 |
| Cp6 | 58 | Ad-C | 24 | Cp6-C48 | | KEYLNKIQNSLSTEW (29) | 45 |
| Cp9 | 61 | Ad-C | 128 | Cp9-C60 | 365-379 | EKKICKMEKCSSVFN (30) | 39 |
| Cp9 | 01 | Ad-CA | 39 | Cp9-C62 | 373-387 | KCSSVFNVVNSSIGL (31) | 116 |
| Cp9 | 08 | Ad-CA | 142 | Cp9-C63 | 377-391 | VFNVVNSSIGLIMVL (32) | 109 |
| Cp9 | 61 | Ad-C | 128 | Cp9-C63 | | VFNVVNSSIGLIMVL (33) | 80 |
| Cp9 | 08 | Ad-CA | 142 | Cp9-C64 | 381-395 | VNSSIGLIMVLSFLF (34) | 91 |
| Cp9 | 01 | Ad-CA | 39 | Cp9-C65 | 383-397 | SSIGLIMVLSFLFLN (35) | 46 |

TABLE 2 -continued

ELISpot IFN-γ activity of CSP peptide pools and individual 15-mer peptides within these pools[1]

| Pool | Vol. | Vaccine | Pool sfc/m | 15 mer peptide | AA No. | Sequence (SEQ ID NO.) | 15 mer sfc/m |
|------|------|---------|------------|----------------|--------|-----------------------|--------------|
| Cp9 | 02 | Ad-CA | 16 | Cp9-C65 | | SSIGLIMVLSFLFLN (36) | 44 |
| Cp9 | 08 | Ad-CA | 142 | Cp9-C65 | | SSIGLIMVLSFLFLN (37) | 62 |

[1] CSP peptide pools Cp1, Cp2, Cp6 and Cp9 the individual 15 mer peptides within each of these pools were tested in ELISpot. 15 individual 15 mer peptides of the 26 15 mer peptides elicited positive recall responses from volunteers immunized with Ad-CA and AD-C. Peptides Cp1-C3, Cp1-C4, Cp2-C12, Cp2-C13, Cp6-C48, Cp9-C63 and Cp9-C65 recalled responses with more than one volunteer. Recall responses to the same 15 mer varied using different volunteers and did not appear to be dependent on whether Ad-CA or Ad-C-immunized volunteers were tested.

EXAMPLE 3

Prediction of Class I-Restricted Epitopes

NetMHC was used to predict HLA A- and HLA B-restricted epitopes within the 15mers active in the ELISpot assay with the strongest binding affinities for the HLA alleles of the corresponding volunteer used in each ELISpot assay (Table 3).

TABLE 3

Predicted CD8+ T cell-restricted epitopes specific for each volunteer within CSP 15 mer Peptides[1]

| 15 mer Peptide | Vol.[2] | Predicted epitope (SEQ ID NO) | AA[3] No. | $IC_{50}$ nM | HLA allele group | HLA supertype | Epitope No. |
|----------------|---------|-------------------------------|-----------|--------------|------------------|---------------|-------------|
| Cp1-C3 | 58 | SVSSFLFVEALFQEY (38) | 13-22 | 258 | A*02:01 | A02 | E1 |
|  | 05 | SVSSFLFVEALFQEY (39) | 15-23 | 50 | A*01:01 | A01 | E2 |
|  | 69 | SVSSFLFVEALFQEY (40) | 15-23 | 68 | B*35:01 | B07 | E2 |
| Cp1-C4 | 12 | FLFVEALFQEYQCYG (41) | 14-23 | 226 | A*30:02 | A01 | E3 |
|  | 01 | FLFVEALFQEYQCYG (42) | 13-22 | 258 | A*02:01 | A02 | E1 |
|  | 69 | FLFVEALFQEYQCYG (43) | 15-23 | 68 | B*35:01 | B07 | E2 |
| Cp1-05 | 58 | EALFQEYQCYGSSSN (44) | 18-27 | 2174 | A*02:01 | A02 | E4 |
| Cp1-C6 | 58 | QEYQCYGSSSNTRVL (45) | 23-32 | 11714 | A*02:01 | A02 | E5 |
| Cp2-C8 | 49 | SSNTRVLNELNYDNA (46) | 32-40 | 4075 | B*15:03 | B27 | E6 |
| Cp2-C10 | 41 | ELNYDNAGTNLYNEL (47) | 40-48 | 321 | B*35:01 | B07 | E7 |
| Cp2-C12 | 12 | TNLYNELEMNYYGKQ (48) | 47-56 | 25 | A*30:02 | A01 | E8 |
|  | 01 | TNLYNELEMNYYGKQ (49) | 49-57 | 468 | B*44:02 | B44 | E9 |
| Cp2-C13 | 12 | NELEMNYYGKQENWY (50) | 54-63 | 132 | A*30:02 | A01 | E10 |
| Cp6-C47 | 61 | DKHIKEYLNKIQNSL (51) | 319-327 | 27 | A*02:01 | A02 | E11 |
| Cp6-C48 | 41 | KEYLNKIQNSLSTEW (52) | 319-327 | 27 | A*02:01 | A02 | E11 |
|  | 05 | KEYLNKIQNSLSTEW (53) | 319-327 | 83 | B*08:01 | B08 | E11 |
|  | 58 | KEYLNKIQNSLSTEW (54) | 319-327 | 27 | A*02:01 | A02 | E11 |
| Cp9-C60 | 61 | EKKICKMEKCSSVFN (55) | 371-379 | 2353 | B*44:02 | B44 | E12 |
| Cp9-C62 | 01 | KCSSVFNVVNSSIGL (56) | 376-385 | 470 | A*02:01 | A02 | E13 |
| Cp9-C63 | 08 | VFNVVNSSIGLIMVL (57) | 379-388 | 70 | A*68:02 | A02 | E14 |
|  | 61 | VFNVVNSSIGLIMVL (58) | 384-391 | 2083 | A*02:01 | A02 | E15 |

TABLE 3 -continued

Predicted CD8+ T cell-restricted epitopes specific for each volunteer within CSP 15 mer Peptides[1]

| 15 mer Peptide | Vol.[2] | Predicted epitope (SEQ ID NO) | AA[3] No. | IC$_{50}$ nM | HLA allele group | HLA supertype | Epitope No. |
|---|---|---|---|---|---|---|---|
| Cp9-C64 | 08 | VNSSIGLIMVLSFLF (59) | 382-391 | 294 | A*68:02 | A02 | E16 |
| Cp9-C65 | 01 | SSIGLIMVLSFLFLN (60) | 387-396 | 53 | A*02:01 | A02 | E17 |
|  | 02 | SSIGLIMVLSFLFLN (61) | 387-396 | 53 | A*02:01 | A02 | E17 |
|  | 08 | SSIGLIMVLSFLFLN (62) | 387-396 | 816 | A*68:02 | A02 | E17 |

[1]The 15 mer peptides that were recognized by the volunteers (Table 2) were analyzed by NetMHC to predict affinity HLA binding by minimal CD8+ T cell epitopes within each 15-mer. Those minimal epitopes with the strongest binding affinities for the HLA alleles of each volunteer were selected. Each minimal epitope was specific for a known HLA allele within each supertype. The Table shows the minimal epitopes that are underlined and in bold.
[2]Vol. = volunteer
[3]AA = amino acid number A total of 17 minimal epitopes were predicted, of which 12 were predicted to be strong binders (IC$_{50}$<500 nM) and four were predicted to be weak binders (IC$_{50}$ 500-5000 nM). For one peptide recalling ELISpot responses, Cp1-C6, NetNHC identified an epitope (E5) where the IC$_{50}$ (>5000 nM) was too low to confirm predicted binding. In a previous study mapping AMA1 epitopes, NetMHC predicted that 11 of 14 epitopes recalling ELISpot responses were strong binders (IC$_{50}$<500 nM), suggesting that NetNHC may successfully predict binders in approximately 70-80% of epitopes (Nielsen, et al., Protein Sci, 12: 1007-17 (2003); Lundegaard, et al., Nucleic Acids Res, 36 Web Server issue): W509-12 (2008)).

The predicted epitopes were numbered E1-E17 in sequence from the N-terminal end of CSP. Three 15mer peptides (Cp1-C3, Cp2-C12, and Cp9-C63) contained two predicted minimal epitopes and one 15mer peptide (Cp1-C4) contained three predicted minimal epitopes, and E1 and E2 overlapped peptides Cp1-C3 and Cp1-C4 (Table 3). In addition, some epitopes overlapped each other: E1, E2, and E3; E4 and E5; E8, E9 and E10; and E12, E13, E14, E15, E16, and E17. The predicted epitopes were 8mers (E15), 9mers (E2, E6, E7, E9, E11, E12,) and 10mers (E1, E3, E4, E5, E8, E10, E13, E14, E16, E17). Ten predicted epitopes were from the N-terminal region (E1 aa 13-22; E2 aa 15-23; E3 aa 14-23; E4 aa 18-27; E5 aa 23-32; E6 aa 32-40; E7 aa 40-48; E8 aa 47-56; E9 aa 49-57; and E10 aa 54-63) and seven epitopes were from the C-terminal region (E11 aa 319-327; E12 aa 371-379; E13 aa 376-385; E14 aa 379-388; E15 aa 384-391; E16 aa 382-391; and E17 aa 387-396).

While different HLA A or B alleles may share common binding epitope motifs that are used to group into HLA supertypes (Sidney, et al., BMC Immunol., 9: 1 (2008); Sette, and Sidney, Current Opin. Immunol., 10: 478-82 (1998)), some class I-restricted malaria epitopes are promiscuous (Doolan, et al., Immunity, 7: 97-112 (1997)). Two epitopes were found to be restricted by different HLA supertypes (Table 3): E2 was predicted to be restricted by both A*01:01 allele group (A01 supertype) and B*35:01 allele group (B07 supertype), and E11 was predicted to be restricted by A*02:01 allele group (A02 supertype) and B*08:01 allele group (B08 supertype), supporting recent meta-analyses (Doolan, et al., Immunity, 7: 97-112 (1997); Vaughan, et al., Parasite Immunol., 31: 78-97 (2009); Rao, et al., Immunogenetics, 63: 691-701 (2011)). In addition, E17 was restricted by two allele groups, A*02:01 and A*68:02 that are of the same A02 supertype. The remaining epitopes were predicted to be restricted by single HLA allele groups: E1, E4, E5, E13, and E15 by A*02:01; E14 and E16 by A*6802 (A02 supertype); E3, E8 and E10 by A*3002 (A01 supertype); E6 by B*1503 (B27 supertype); E7 by B*3501 (B07 supertype); E9 and E12 by B*4402 (B44 supertype).

Epitopes predicted to bind to A03, were predicted for 7 of the 8 volunteers expressing this HLA type but were not tested. No A03 epitope was predicted for the eight volunteer, v69. Likewise, no epitopes were predicted to bind to B58 (expressed by v12 and v156) and also for B62 (expressed by v40 and v68, as shown in Table 1).

EXAMPLE 4

ELISpot of Synthesized Minimal Peptides

The next step was to synthesize and test predicted epitopes in ELISpot to verify their recognition by volunteers expressing HLA alleles compatible to the predicted HLA-restriction of these epitopes. Five predicted putative epitopes were selected that matched the HLA alleles expressed by volunteers from whom we had sufficient cells. These were E1, E2, E3, E13, and E17. In addition, five new epitopes were synthesized that were predicted by NetMHC to match the volunteers, for which PBMC was available, but were not identified in the original epitope analysis using 15mer peptides, as in Table 3. These were numbered E17a (as it is contained within E17), E18, E19, E20 and E21. Nine of the 17 volunteers listed in Table 1 were used in these assays and had been immunized with Ad-CA or Ad-C.

Each predicted epitope was tested in ELISpot and the results of ELISpot activities and NetMHC predictions are shown in Table 4. In some assays epitopes that were not predicted to bind to that volunteer were also tested. Each synthesized predicted epitope was tested with the original peptide pool from which it was derived. Some epitopes were tested twice and for E13a and E20 there were only sufficient cells to test the peptide pool in one assay.

TABLE 4

ELISpot IFN-γ activity of CSP peptide pools and predicted 8-10 mer epitopes within these pools[1]

| Pool | Pool Vol. | Epitope sfc/m | Epitope No. | Epitope Sequence (SEQ ID NO) | AA No. (SEQ ID NO.) | HLA allele group | HLA supertype | $IC_{50}$ nM | Epitope sfc/m |
|---|---|---|---|---|---|---|---|---|---|
| *Predicted Epitopes (from Table 3)* | | | | | | | | | |
| Cp1 | 58 | ND[2] | E1 | FLFVEALFQE | 13-22 (1) | A*02:01 | A02 | 258 | 49 |
| Cp1 | 156 | 126 | E1 (E1a) | FLFVEALFQE | 13-21 (1) | A*03:01 | A03 | 4312 | 105 |
| Cp1 | 69 | ND | E2 | FVEALFQEY | 15-23 (3) | B*35:01 | B07 | 68 | 268 |
| Cp1 | 127 | 69 | E2 | FVEALFQEY | 15-23 (3) | A*01:01 | A01 | 63 | 89 |
| Cp1 | 69 | ND | E3 | LFVEALFQEY | 14-23 (4) | A*30:02 | A01 | 63 | 259 |
| Cp1 | 69 | ND | E3 (E2) | LFVEALFQEY | 15-23 (4) | B*35:01 | B07 | 68 | 259 |
| Cp1 | 127 | 69 | E3 (E2) | LFVEALFQEY | 15-23 (4) | A*01:01 | A01 | 63 | 99 |
| Cp9 | 37 | 79 | E13 | SVFNVVNSSI | 376-385 (5) | A*68:02 | A02 | 18 | 28 |
| Cp9 | 58 | 13 | E13 | SVFNVVNSSI | 376-385 (5) | A*02:01 | A02 | 470 | 80 |
| Cp9 | 40 | 43[@,4] | E13a | SVFNVVNSSI | 377-385 (5) | A*23:01 | A24 | 1801 | 104, 72 |
| Cp9 | 156 | 64 | E17 (E17a) | LIMVLSFLFL | 387-395 (63) | A*29:02 | A01A24 | 190 | 156 |
| *New Predicted Epitopes* | | | | | | | | | |
| Cp9 | 37 | 79 | E17a | LIMVLSFLF | 387-395 (7) | B*15:03 | B27 | 111 | 55, 38 |
| Cp9 | 40 | 43 | E17a | LIMVLSFLF | 387-395 (7) | A*23:01 | A24 | 282 | 290, 166 |
| Cp1 | 63 | ND | E18 (E18a) | AILSVSSFLF | 6-14 (64) | A*24:03 | A24 | 5375 | 41 |
| Cp1 | 125 | 27 | E19 | SVSSFLFVEA | 9-18 (9) | NP[3] | NP | NP | 33 |
| Cp1 | 37 | 36[@] | E20 | SFLFVEALF | 12-20 (10) | A*23:01 | A24 | 104 | 53, 53 |
| Cp1 | 40 | 163[@] | E20 | SFLFVEALF | 12-20 (10) | A*23:01 | A24 | 104 | 313, 197 |
| Cp1 | 68 | ND | E20 | SFLFVEALF | 12-20 (10) | A*24:02 | A24 | 104 | 34 |
| Cp1 | 156 | 120 | E20 | SFLFVEALF | 12-20 (10) | NP | NP | NP | 240 |
| Cp9 | 125 | 58 | E21 | IMVLSFLFL | 388-396 (11) | NP | NP | NP | 29 |

[1]Five predicted epitopes from Table 3, and five new predicted epitopes, were tested with volunteers immunized with Ad-CA or Ad-C. Activity was measured as sfc/m. E1a, E2a, E13a, E17a and E18a designate 9 mer sequences, underlined, contained within E1, E2, E13, E17 and E18 epitopes respectively.
[2]ND = Not Done.
[3]NP = Not Predicted
[4]@The response to the peptide pool was not done in the second assay.

As illustrated in Table 4, the epitope E1 (FLFVEALFQE) (SEQ ID No. 1) was active using the same volunteer (v58) that was tested with the parent Cp1-C3 15mer (Table 3), and NetMHC predicted the strongest binding to A*02:01 (A02 supertype). E1 was also positive with v156 who does not express A*02:01; however, E1 contains the 9mer FLFVEALFQ (SEQ ID No. 2) (epitope E1a in Table 4) that NetMHC predicted bound weakly ($IC_{50}$=4312 nM) with A*03:01 (A03 supertype) that is expressed by v156. E2 (FVEALFQEY) (SEQ. No. 3) was active using the same volunteer (v69) that was tested with the parent 15mers Cp1-C3 and Cp1-C4 (Table 3), and NetMHC predicted binding to B*35:01 (B07 supertype). In addition E2 was active with v127 and NetMHC predicted binding to A*01:01 (A01 supertype). E2 was also predicted to bind to A*01:01 using the Cp1-C3 15mer but for a different volunteer (v05, Table 3). Therefore we conclude that E2 is restricted by two allele groups, B*35:01 and A*01:01 that belong to different supertypes, B07 and A01 respectively. E3 (LFVEALFQEY) (SEQ. No. 4) could not be tested with v12 that was positive with the parent Cp1-C4 15mer (Table 3). However, E3 was active with v69 and NetMHC predicted binding to A*30:02 (A01 supertype). E3 contains the 9mer E2 sequence (FVEALFQEY) (SEQ. No. 3) that NetMHC predicted to bind to B*35:01 that is also expressed by v69. E3 was also positive with v127 and NetMHC predicted that the E2 sequence within E3 bound to A*01:01-restricted, matching v127. E13 (SVFNVVNSSI) (SEQ. No. 5) was positive with v58 and was predicted to bind to A*02:01 (A02 supertype), and was also positive with v37 and predicted to bind with A*68:02 (Table 4) that like A*02:01 is part of the A02 supertype. E13 was also positive with v40 and NetMHC predicted that a 9mer sequence VFNVVNSSI (SEQ. No. 6) contained within E13 (labeled E13a, Table 4) may bind (weakly) to A*23:01 (A24 supertype). E17 (LIMVLSFLFL) (SEQ. No. 63) could not be tested with v01, v02, and v08 who responded to the parent Cp9-C65 15mer (Table 2). E17 was predicted as A*02:01-restricted for v01 and v02 (Table 3) and also as A*68:02-restricted (A02 supertype) for v08 with low binding (IC50, 816). E17 was positive with v156 who does not express A*02:01 or A*68.02. However, E17 contains the 9mer sequence LIMVLSFLF (E17a) (SEQ ID No. 7) and NetMHC predicted this sequence binds to A*29:02 (A01A24 supertype) that is expressed by v156.

Also illustrated in Table 4, E17a (LIMVLSFLF) (SEQ ID No. 7) was recognized by v37 and NetMHC predicted binding to B*15:03 (B27 supertype). E17a was also positive with v40 and NetMHC predicted binding to A*23:01 (A24 supertype). Therefore, we conclude that E17a ELISpot activity is restricted by three allele groups, A*29:02, B*15: 03 and A*23:01 that are members of three HLA supertypes, A01A24, B27 and A24, respectively. E18 (AILSVSSFLF)

(SEQ ID No. 64) was predicted as an A*23:01 restricted epitope using v40, but PBMC were not available from v40; however, E18 was positive with v63, which does not express A*23:01, but NetMHC predicted binding low/negative ($IC_{50}$5375) binding affinity of an epitope contained within E18 (E18a, AILSVSSFL) (SEQ ID No. 8) for A*24:03 that is expressed by v63. Both A*23:01 and A*24:03 are members of the A24 supertype. E19 (SVSSFLFVEA) (SEQ ID No. 9) was predicted to be A*68:02-restricted (A02 supertype) using v52, but PBMC were not available from this volunteer. E19 was moderately active with v125 but NetMHC could not predict binding to HLA alleles expressed by v125. However, v125 also expresses the A02 supertype (Table 1) and it is possible therefore that E19 may be sufficiently degenerate to bind to the A02 supertype expressed by v125. E20 (SFLFVEALF) (SEQ ID No. 10) was positive with v37 and v40 and NetMHC predicted binding to A*23:01 with v37. Although NetMHC did not return a prediction for v40, we assume that since v40 also expresses the A*23:01 allele group (Table 1), E20 is also restricted by A*2301 (A24 supertype) expressed by this volunteer. E20 was also moderately positive with v68 and NetMHC predicted binding to A*24:02 that like A*23:01 is a member of the A24 supertype. In addition, E20 was also positive with v156 and NetMHC could not predict binding to those HLA alleles expressed by v156. It is possible that E20 may be sufficiently degenerate to bind to allele groups expressed by v156 an A01A24 supertype. E21: (IMVLSFLFL) (SEQ ID No. 11) was predicted as binding to B*1503 using v37 from whom cells were not available. E21 gave a low to modest response against v125 but NetMHC could not predict binding to these HLA allele groups expressed by this volunteer and may also be an example of epitope degeneracy when binding cannot predicted by NetMHC.

The peptides in Table 4 are also listed in Table 5 summarizing the epitopes and their corresponding sequence identification number.

TABLE 5

| Epitope | SEQ ID No. |
|---------|------------|
| E1      | 1          |
| E1a     | 2          |
| E2      | 3          |
| E3      | 4          |
| E13     | 5          |
| E13a    | 6          |
| E17a    | 7          |
| E18a    | 8          |
| E19     | 9          |
| E20     | 10         |
| E21     | 11         |

EXAMPLE 5

Confirmation of MHC Class I-Restriction

To further evaluate the predicted epitopes, ELISpot depletion assays were performed using PBMC from four volunteers stimulated with six predicted and tested epitopes. CD8+ T cell depletion reduced responses to Cp1 and Cp9 by 82%100%. The results are shown in Table 6.

TABLE 6

ELISpot IFN-γ activity of CSP predicted epitopes after depletion of CD4+ and CD8+ T cells compared with ICS CD8+ and CD4+ T cell IFN-γ activity

| Vol. | Pool | Epitope No. (SEQ ID NO.) | Sequence | AA No. | HLA allele group | Control dept. sfc/m | CD8+ depl. sfc/m (%)* | CD4+ depl. sfc/m (%)* | CD8+ %** | CD4+ %** |
|------|------|--------------------------|----------|--------|------------------|---------------------|-----------------------|-----------------------|----------|----------|
| V40  | Cp1  |                          |          |        |                  | 97                  | 5 (−95%)              | 82 (−15%)             | 0.44     | 0.02     |
|      |      | E20 (10)                 | SFLFVEALF | 12-20 | A*23:01          | 254                 | 15 (−94%)             | 226 (−11%)            | 0.37     | 0.04     |
|      |      | E13a (6)                 | SVFNVVNSSI | 377-385 | A*23:01        | 86                  | 38 (−56%)             | 43 (−50%)             | 0.12     | 0.01     |
|      |      | E17a (7)                 | LIMVLSFLF | 387-395 | A*23:01         | 236                 | 23 (−90%)             | 210 (−11%)            | 0.54     | 0.02     |
| V69  | Cp1  |                          |          |        |                  | 334                 | 6 (−98%)              | 312 (−7%)             | 0.53     | 0.01     |
|      |      | E2 (3)                   | FVEALFQEY | 15-23 | B*3501           | 296                 | 8 (−97%)              | 254 (−15%)            | 0.48     | 0.00     |
| V125 |      | E19 (9)                  | SVSSFLFVEA | 9-18  | NP               | 79                  | 72 (−9%)              | 17 (−78%)             | 0.06     | 0.02     |
| V156 | Cp1  |                          |          |        |                  | 133                 | 0 (−100%)             | 135 (+2%)             | 0.33     | 0.01     |
|      |      | E20 (10)                 | SFLFVEALF | 12-20 | NP               | 213                 | 29 (−86%)             | 273 (+28%)            | 0.25     | 0.01     |
|      |      | E1a (2)                  | FLFVEALFQE | 13-21 | A*03:01         | 245                 | 91 (−73%)             | 215 (−12%)            | 0.34     | 0.03     |
|      | Cp9  | E17a (7)                 | LIMVLSFLF | 387-395 | A*29:02         | 307                 | 85 (−82%)             | 264 (−18%)            | 0.26     | 0.01     |

*The percent change in ELISpot activity is shown after depetion of CD4+ or CD8+ T cells.

**The per cent of CD8+ or CD4+ T cells expressing IFN-γ.

based on predicted binding to A*68:02 using v52 depl. = depletion

Vol. = number sfc/m = spot forming cells/million

NP = Not Predicted

The percent reduction after CD8+ T cell depletion varied from 73%-97% with epitopes E1a, E2, E17a and E20, but only by 56% for E13a and 9% with E19 (Table 6). However, ICS assays CD8+ T cell recall responses were positive, and CD4+ T cell recall responses were negative, for Cp1 and Cp9, and E1a, E2, E13a, E17a and E20, although the frequency of CD8+ T cell responses for E19 was weakly positive (0.06%). Therefore we conclude that these six predicted epitopes were minimal class I epitopes targeted by CD8+ T cells.

Based on strong reactivity against specific 15mer peptides within peptide pools, seventeen 8-10mer epitopes (E1-E17) were initially identified using NetMHC predictions of binding to the HLA A and B alleles expressed by a panel of Ad-CA and Ad-C-immunized volunteers (Tables 2 and 3). The results of the epitopes that were identified and confirmed as targets for CD8+ T-cells using ELISpot and ELISpot-depletion/ICS studies are summarized in Table 7.

In addition, E20 was positive in ELISpot with v156 for which no predictions could be made, suggesting that E20 is sufficiently degenerate to bind to the alleles expressed by v156. This promiscuity of restriction is likely underestimated due to the limited availability of PBMC from only 17 volunteers used in this study. When NetMHC was used to predict all restrictions of epitopes within Cp1, Cp2, Cp6 and Cp9, many more potential restrictions were identified that could not be evaluated in this study.

Initially using NetMHC, 17 epitopes were predicted to fall within fifteen individual 15mer peptides derived from 4 most active CSP pools. Among these 17, ten were localized in the N-terminal region, and seven were localized to the C-terminal region (Table 3). Among the 11 epitopes which were synthesized and confirmed to recall responses in ELISpot assays, seven epitopes were localized to the N-ter-

TABLE 7

Summary of predicted and confirmed minimal CSP epitopes

| 15 mer peptide | Epitope No. (SEQ ID NO.) | Sequence | AA No. | 15 mer ELISpot activity | Epitope ELISpot activity | Dep./ICS | HLA allele group | HLA supertype |
|---|---|---|---|---|---|---|---|---|
| Cp1-C3 | E1 (1) | FLFVEALFQE | 13-22 | + | + |  | A*02:01 | A02 |
|  | E1a (2) | FLFVEALFQ | 13-21 |  | + | + | A*03:01 | A03 |
|  | E2 (3) | FVEALFQEY | 15-23 | + | + |  | A*01:01 | A01 |
|  | E2 (3) | FVEALFQEY | 15-23 | + | + | + | B*35:01 | B07 |
| Cp1-C4 | E3 (4) | LFVEALFQEY | 14-23 | + | + |  | A*30:02 | A01 |
| Cp9-C62 | E13 (5) | SVFNVVNSSI | 376-385 | + | + |  | A*02:01 | A02 |
|  |  |  |  |  | + |  | A*68:02 | A02 |
|  | E13a (6) | VFNVVNSSI | 377-385 |  | + | + | A*23:01 | A24 |
| Cp9-C65 | E17a (7) | LIMVLSFLF | 387-395 |  | + | + | A*23:01 | A24 |
|  |  |  |  |  | + | + | A*29:02 | A01A24 |
|  |  |  |  |  | + |  | B*15:03 | B27 |
| Cp1-C1 | E18a (8) | AILSVSSFL | 6-14 |  | + |  | A*24:03% | A24 |
| Cp1-C2 | E19 (9) | SVSSFLFVEA | 9-18 |  | + | + | NP | NP |
| Cp1-C3 | E20 (10) | SFLFVEALF | 12-20 |  | + | + | A*23:01 | A24 |
|  |  |  |  |  | + |  | A*24:02 | A24 |
|  |  |  |  |  | + |  | NP | NP |
| Cp9-C65 | E21 (11) | IMVLSFLFL | 388-396 |  | + |  | NP | NP |

+Positive activity of the 15 mer and predicted epitope in ELISpot, or recall of CD8+ T cells in ELISpot depletion (Dep) or intracellular staining/flow cytometry (ICS).
NetMHC predicted minimal epitope within the 15 mer was active in ELISpot, or the synthesized epitope was active in ELISpot or ELISpot depletion and ICS assays.
%NetMHC binding affinity was >5000 nM, so this restriction cannot be assigned with certainty.
No. = number
NP = Not Predicted Eleven of the synthesized epitopes that were evaluated demonstrated activity in ELISpot assays (E1, E1a, E2, E3, E13, E13a, E17a, E18a, E19, E20 and E21). The restricted availability of PBMC from immunized volunteers only allowed six of these epitopes, E1a, E2, E13a, E17a, E19 and E20 to be confirmed as recalling CD8+ T cell responses.

This study supports previous findings that some class I epitopes are sufficiently degenerate to bind to more than one allele group or supertype (Doolan, et al., Immunity, 7: 97-112 (1997)). As shown in Table 6, E2 was restricted by A*01:01 (A01 supertype) and B*35:01 (B07 supertypes), and E17a was restricted by A*23:01 (A24 supertype), A*29:02 (A01A24 supertype) and B*1503 (B27 supertype). E13 was restricted by two allele groups of the A02 supertype (A*02:01 and A*68:02), and E20 was restricted by two allele groups of the A24 supertype (A*23:01 and A*24:02).

minal region (E1, E1a, E2, E3, E18a, E19 and E20) and four epitopes were localized to the C-terminal (E13, E13a, E17a and E21) regions.

EXAMPLE 6

Recombinant Construct Comprising One or More CSP Epitopes Useful an Anti-Anti-Malarial Immunogen The inventive recombinant construct has utility in the development of adenovirus-vectored vaccines (Ad-C and Ad-CA) designed to induce CD8+ T cell responses targeting pre-erythrocytic stage antigens. This approach is based on data indicating that CD8+ T cell responses are associated with protection against liver stage parasites in animal models and in humans (Sedegah, et al., PLoS One, 6: e24586 (2011); Tamminga, et al., PLoS One, 6: e25868 (2011)). The aim of this study was to better understand the immune responses elicited by CSP by mapping MHC class I restricted epitopes to aid the development of a broadly protective malaria vaccine for genetically diverse populations. To date, only a few class I-restricted epitopes have been described for this antigen (Calvo-Calle, et al., J. Immunol., 159: 1362-73 (1997); Doolan, et al., Immunity 7: 97-112 (1997); Aidoo, et al., Lancet, 345: 1003-7 (1995); Hill, et al., Nature, 352: 595-600 (1991)). We have previously demonstrated that CSP peptide pools containing overlapping 15mer peptides recalled CD8+ T cell responses using ELISpot and ICS (Sedegah, et al., PLoS One, 6: e24586 (2011); Tamminga, et al., PLoS One, 6: e25868 (2011)), and we decided to identify class 1-restricted 8-10mers within the four most active peptide pools Cp1, Cp2, Cp6 and Cp9. We used an integrated approach where the computer algorithm NetMHC (Lundegaard, et al., Nucleic Acids Res., 36 (web server issue):W509-12 (2008)) was used to predict putative minimal class 1-restricted epitopes within 15mer CSP peptides that were active in ELISpot assay using Ad-C and Ad-CA immunized volunteers. Most HLA-restricted peptides have binding affinities of less than 50 nM, although some may bind in the 50-500 nM range (Sette, et al., Mol. Immunol., 31: 813-22 (1994)).

The predicted epitopes were synthesized and tested them using PBMCs from volunteers from the same clinical trials. Using this approach, 11 predicted HLA class I restricted minimal epitopes were identified. Six were confirmed to be recognized by CD8+ T cells using ELISpot depletion and ICS studies. A major constraint to these studies was the availability of PBMC from immunized volunteers. All the 11 epitopes confirmed in this study were novel and to our knowledge have not been previously described (Vaughan, et al., Parasite Immunol., 31: 78-97 (2009)).

While peptide binding to class I MHC molecules is required for T cell recognition, many peptides that bind with high affinity are not recognized by T cells (Sidney, et al., BMC Immunol., 9: 1 (2008)). Therefore, an attempt was made to demonstrate that these predicted epitopes were recognized by CD8+ T cells from Ad-C and Ad-CA-immunized volunteers. NetMHC was utilized to predict epitopes that likely matched the HLA alleles of volunteers for which PBMC were available. Despite the restricted availability of PBMC from immunized volunteers, six of the 11 epitopes that were active in ELISpot were demonstrated to recall CD8+ T cell responses. Since most class I-binding peptides are usually 8-10 amino acids, while class II peptides range from 12 to 24 residues (Doolan, et al., Immunity, 7: 97-112 (1997); Chicz, et al., J. Exp. Med., 178: 27-47 (1993)), it is likely that all 11 epitopes are class I-restricted.

Predicated on earlier studies with *P. falciparum* epitopes, including CSP, it was presumed that there is a high degree of degeneracy such that minimal 8-10mer peptides bind to more than one HLA allele within different supertypes (Doolan, et al., Immunity, 7: 97-112 (1997)). This was shown by E2 that was predicted to bind to A*01:01 and B*35:01, members of different HLA supertypes (A01 and B07), and E11a that was predicted to bind to A*23:01, A*2902 and B*15:03 (A24, A01A24 and B27 supertypes, respectively). In addition, E13 was predicted to bind to A*02:01 and A*68:02 (both members of the A02 supertype), and E20 was predicted to bind to A*23:01 and A*24:02 (both members of the A24 supertype). This is consistent with findings that many different HLA alleles overlap in their peptide-binding properties (Sidney, et al., J. Immunol., 154: 247-59 (1995); Sette and Sidney, Immunogenetics, 50: 201-12 (1999); Doolan, et al., Immunity, 7: 97-112 (1997); Sidney, et al., BMC Immunol., 9: 1 (2008); Sette and Sidney, Current Opin. Immunol., 10: 478-82 (1998); Sidney, et al., Hum. Immunol., 45: 79-93 (1996); Sidney, et al., J. Immunol., 157: 2480-90 (1996)).

Further examples were found when NetMHC predictions of the HLA-restrictions of peptides spanning the full length of CSP were analyzed suggesting that this HLA supertype promiscuity may be more extensive than demonstrated here. Promiscuous class I-restricted epitopes that recognize different HLA supertypes have been reported for viral diseases suggesting that many epitopes can be presented on different HLA alleles (Frahm, et al., J. Virol., 78: 2187-200 (2004); Frahm, et al., J. Immunol., 37: 2419-33 (2007)).

In other studies, certain allele pairs frequently shared epitopes (Frahm, et al., J. Immunol., 37: 2419-33 (2007)); however, the small number of epitopes identified in this study precluded such an analysis. As with class I epitopes studied here, CSP DR epitopes have been shown to be promiscuous. Recently, class II-restricted epitopes have been assigned to seven supertypes, reflecting a more pronounced dependence on backbone interactions than on peptide anchor residues (Greenbaum, et al., Immunogenetics, 63: 325-35 (2011)). This provides encouraging evidence that a CSP adenovirus-vectored vaccine may be immunogenic in genetically diverse populations.

Recent studies have suggested that the N-terminal region folds over and protects the C-terminal region of CSP, exposing only the N-terminal and repeat regions to binding antibodies (Coppi, et al., J. Exp. Med. 208: 341-56 (2011)). Surface location has been suggested to increase accessibility of HIV T-cell epitopes to the antigen-processing pathway (Surman, et al., PNAS (USA, 98: 4587-92 (2001); Sijts, et al., J. Immunol., 164: 4500-6 (2000)), and CSP peptide pools containing peptides spanning the N-terminal recalled strong CD8+ T cell responses in Ad-C and Ad-CA-immunized volunteers.

However, CSP peptide pools containing peptides spanning the C-terminal region also elicited similar strong CD8+ T cell responses, indicating that induction of strong CD8+ T cell responses is not related to CSP sequence localization. Part of the N-terminal region containing E1, E1a, E2, E3, E18, E19 and E20 is proteolytically cleaved during sporozoite invasion, while truncated CSP containing E13, E13a, E17a and E21 is carried into the hepatocyte (Coppi, et al., J. Exp. Med., 208: 341-56 (2011); Hollingdale, M. R., Prog Allergy, 41: 15-48 (1988)), suggesting that N- and C-terminal epitopes may be processed and presented to the immune system by different mechanisms.

Amino acid polymorphism may also be associated with surface accessibility or immune pressure (Thera, et al., PLoS One, 3: e1465 (2008); Zevering, et al., Immunology, 94: 445-54 (1998); Escalante, et al., Mol. Biochem. Parasitol., 125: 83-90 (2002)).

EXAMPLE 7

Use of Epitopes in Vaccine Candidate Evaluation and as Components in Immunogenic Formulations Class I restricted T-cells are important for immunity against liver stage malaria parasites. The regions identified herein are of particular importance. As such, a preferred embodiment is recombinant polypeptide construct, which can be used as a component of an immunogenic composition capable of inducing an immune response in mammals, comprising one or more polypeptides comprising isolated CSP T-cell epitopes, wherein said epitopes have the amino acid sequences selected from the group consisting of SEQ ID Nos. 1-11.

In one embodiment, a recombinant polypeptide construct comprises a polypeptide containing one or more isolated CSP T-cell epitopes with the amino acid sequence of sequences of SEQ ID Nos. 1-11. This recombinant polypeptide construct would not contain the intervening CSP amino acid regions found in the native CSP. Furthermore, the polypeptide can contain more than one copy of any one of the epitopes of SEQ ID No. 1-11. In one embodiment, the recombinant polypeptide construct can contain 1-10 amino acid spacer sequences, separating individual epitopes wherein the said spacers do not contain a T-cell epitope.

An additional embodiment is to enable anti-malaria immunity to as large a demographic population as possible. To this end, this embodiment includes the incorporation of epitopes that further contain specific HLA class I binding motifs encompassing significant portions of population groups. In the current invention, the identified epitopes are restricted by specific HLA allele groups.

Therefore, in a preferred embodiment, a recombinant polypeptide construct, comprising one or more of the epitopes of SEQ ID No. 1-11 or more than one copy of any of the epitopes of SEQ ID No. 1-11, can be utilized as an antigen or expressed from a suitable expression system. In this embodiment, the polypeptide contains the epitopes without the intervening, non-epitopic CSP amino acid regions. Suitable expression systems include DNA plasmid expression systems or viral expression systems. It is advantageous to develop peptides that are recognized in conjunction with as many important HLA alleles as possible in or order to afford protection to as large a population as possible. Therefore, it is contemplated, in another preferred embodiment, that the inventive polypeptides could be utilized with other HLA-restricted polypeptides.

A further embodiment of the invention is a method of inducing an immune response utilizing an immunogenic composition containing one or more the peptides of SEQ ID No. 1 through 11. The method comprises administering the recombinant polypeptide construct, with or without adjuvant, either as a subunit vaccine or by expressing the peptides as a component of a DNA or viral expression system.

In one embodiment, the contemplated method includes administration of one or more priming immunizations or one or more boosting immunizations of a composition comprising a recombinant polypeptide construct containing one or more of the epitopes of SEQ ID Nos. 1-11. In another embodiment, the composition comprises one or more isolated nucleic acid molecules inserted into suitable expression vectors. The nucleic acid molecules in this embodiment encode a recombinant polypeptide construct containing one or more epitopes with the amino acid sequences of SEQ ID Nos. 1-11. The embodiment also contemplates that one or more priming or one or more boosting immunizations could comprise administration of irradiated sporozoites.

It is contemplated that suitable expression vectors would be selected from the group consisting of DNA plasmid, alphavirus replicon, adenovirus, poxvirus, adeno-associated virus, cytomegalovirus, canine distemper virus, yellow fever virus and retrovirus. In another embodiment, the priming immunization vector is an alphavirus and the boosting immunization is a non-alphavirus vector. The non-alphavirus vector can be poxvirus, adenovirus, adeno-associated virus and retrovirus. The poxvirus can be cowpox, canarypox, vaccinia, modified vacinia Ankara, or fowlpox. Alternatively, the priming immunization can be comprised of an expression vector that is a DNA plasmid or an adenovirus with the boosting immunization selected from the group consisting of adenovirus, adenovirus that is heterologous to the priming adenovirus, poxvirus and one or more recombinant polypeptide constructs containing one or more epitopes of SEQ ID No. 1-11. Furthermore, the alphavirus replicon can be a preparation selected from the group consisting of RNA replicon, DNA replicon and alphavirus replicon particles. The alphavirus can be Venezuelan Equine Encephalitis Virus, Semliki Forest virus and Sindbis Virus.

In addition to use of the recombinant polypeptide construct as a component of anti-malaria immunogen, the construct can be incorporated into a methods for the evaluation of the efficaciousness of vaccine candidates. Methods evaluating correlates of immunity is an important component in vaccine development. As mentioned above, an important parameter in anti-malaria immunity is induction of anti-Class I restricted T-cell response.

Therefore, one embodiment is the use of the class I restricted epitopes, incorporated into a recombinant polypeptide construct, in a method to screen immunity against vaccine candidates. The method comprises:
  a. Exposing human lymphocytes to one or more recombinant polypeptide constructs containing one or more of the amino acid sequences 1 through 11; and
  b. Determining T-cell response.

Determination of responder T-cell populations can be conducted by any number of methods. In a preferred embodiment, induction of IFN-γ or other T-cell cytokines are measured by ELISpot assay or other in vitro methods.

What is claimed is:

1. A recombinant polypeptide construct comprising the amino acid sequences SEQ ID No. 5, 6 and 7, and one or more amino acid sequences selected from the group consisting of SEQ ID No. 1, 2, 3, 4, 8, 9, 10, and 11, wherein each of the amino acid sequences of SEQ ID No. 5, 6, 7 and on or more amino acid sequences selected from the group consisting of SEQ ID No. 1, 2, 3, 4, 8, 9, 10 and 11 contain a T-cell epitope isolated from *Plasmodium falciparum* circumsporozoite protein and, wherein said amino acid sequences are linked to each other directly or linked to each other via polypeptide spacer sequences, wherein said spacer sequences do not contain a T-cell epitope, and wherein the polypeptide construct is expressed from a DNA or viral expression system.

2. The recombinant polypeptide construct of claim 1, wherein the spacer sequences are amino acid sequences of 1 to 10 amino acids in length.

3. A method of inducing an immune response in a mammal against *Plasmodium falciparum* comprising administering one or more doses of the composition of claim 1.

4. A method of inducing an immune response in a mammal against *Plasmodium falciparum* comprising administering the composition of claim 1 as one or more priming immunizations or one or more boosting immunizations, or both.

5. The method of claim 3, wherein said recombinant polypeptide construct is expressed from a DNA or viral expression vector.

6. The method of claim 3, wherein one or more priming or one or more boosting immunizations comprises irradiated sporozoites.

7. The method of claim 5, wherein said DNA or viral expression vector is selected from the group consisting of DNA plasmid, alphavirus replicon, adenovirus, poxvirus, adeno-associated virus, cytomegalovirus, canine distemper virus, yellow fever virus and retrovirus.

8. The method of claim 7, wherein said priming immunization vector is an alphavirus vector and said boosting immunization is a non-alphavirus vector.

9. The method of claim 7, wherein said priming immunization comprises an expression vector that is a DNA plasmid or an adenovirus and the boosting immunization comprises an expression vector selected from the group consisting of adenovirus, adenovirus heterologous to the priming adenovirus, poxvirus and a recombinant polypeptide construct comprising the amino acid sequences SEQ ID No. 5, 6 and 7, and one or more amino acid sequences selected from the group consisting of SEQ ID No. 1, 2, 3, 4, 8, 9, 10, and 11, wherein each of the amino acid sequences of SEQ ID No. 5, 6, 7 and on or more amino acid sequences selected from the group consisting of SEQ ID No. 1, 2, 3, 4, 8, 9, 10 and 11 contain a T-cell epitope isolated from *Plasmodium falciparum* circumsporozoite protein and, wherein said amino acid sequences are linked to each other directly or linked to each other via polypeptide spacer sequences, wherein said spacer sequences do not contain a T-cell epitope, and wherein the polypeptide construct is expressed from a DNA or viral expression system.

10. The method of claim 8, wherein said alphavirus vector is a preparation is selected from the group consisting of RNA replicon, DNA replicon and alphavirus replicon particles.

11. The method of claim 8, wherein said non-alphavirus expression system is selected from the group consisting of poxvirus, adenovirus, adeno-associated virus and retrovirus.

12. The method of claim 10, wherein the alphavirus is selected from the group consisting of Venezuelan Equine Encephalitis Virus, Semliki Forest Virus and Sindbis Virus.

13. The method of claim 11, wherein the poxvirus is selected from the group consisting of cowpox, canarypox, vaccinia, modified vaccinia Ankara, or fowlpox.

* * * * *